United States Patent [19]

Lison

[11] Patent Number: 4,972,521
[45] Date of Patent: Nov. 27, 1990

[54] PROTECTIVE EYEWEAR

[75] Inventor: Solomon M. Lison, Cape Town, South Africa

[73] Assignee: Negaids (Properietary) Limited, Cape Province, South Africa

[21] Appl. No.: 402,877

[22] Filed: Sep. 5, 1989

[51] Int. Cl.$^5$ ............................................. A61F 9/00
[52] U.S. Cl. ....................................... 2/9; 2/13; 2/432; 2/435; 2/436; 2/439; 2/454; 128/863
[58] Field of Search ............... 2/9, 11, 12, 13, 439, 2/206, 427, 428, 431, 432, 435, 436, 439, 454; 128/858, 863

[56] References Cited

U.S. PATENT DOCUMENTS

| | | | |
|---|---|---|---|
| 857,689 | 6/1907 | Tileston | 2/454 |
| 1,337,036 | 4/1920 | Bergman | 2/12 |
| 1,452,305 | 4/1923 | Mahoney | 2/12 |
| 1,795,866 | 3/1931 | King | 128/863 X |
| 2,227,667 | 1/1941 | Panettiere | 128/863 X |
| 2,247,971 | 7/1941 | Snell | 2/12 |
| 2,409,243 | 10/1946 | Bernheim et al. | 2/454 |
| 2,517,864 | 8/1950 | Fulton | 2/12 |
| 2,541,242 | 2/1951 | Grove | 2/13 |
| 2,907,041 | 10/1959 | Finn | 2/14 |
| 3,241,155 | 3/1966 | Phillips | 2/9 |
| 3,298,032 | 1/1967 | Sielisch | 2/13 |
| 3,828,366 | 8/1974 | Conrad et al. | 2/9 X |
| 4,414,693 | 11/1983 | Brody | 2/435 |
| 4,428,079 | 1/1984 | McKee | 2/174 |
| 4,610,036 | 9/1986 | LaPrairie | 2/12 |
| 4,621,378 | 11/1986 | Hatchman | 2/9 |
| 4,701,965 | 10/1987 | Landis | 2/428 |
| 4,779,291 | 10/1988 | Russell | 2/439 |
| 4,797,956 | 1/1989 | Boyce | 2/431 |
| 4,850,058 | 7/1989 | Cheng | 2/439 |
| 4,852,185 | 8/1989 | Olson | 2/9 |
| 4,867,178 | 9/1989 | Smith | 2/9 X |
| 4,872,465 | 10/1989 | Kuntz et al. | 2/9 X |

FOREIGN PATENT DOCUMENTS 107522  9/1965  Norway ............................... 2/439

Primary Examiner—Werner H. Schroeder
Assistant Examiner—Jeanette E. Chapman
Attorney, Agent, or Firm—Kenyon & Kenyon

[57] ABSTRACT

Protective eyewear is disclosed which comprises a sheet of transparent synthetic plastics material with means for attaching to the wearer's head with a viewing area of said sheet extending across the wearer's eyes. A protrusion extends along the top edge of the sheet, contacts the wearer's forehead in use and holds the viewing area away from the wearer's eyes. Slits are provided in the sheet to improve ventilation and the plastics material is coated with anti-fogging material to prevent misting-up. The slits also make it possible to use the protective eyewear over spectacles.

7 Claims, 2 Drawing Sheets

PROTECTIVE EYEWEAR

FIELD OF THE INVENTION

THIS INVENTION relates to protective eyewear particularly, but not exclusively, for use by surgeons and other medical practitioners.

BACKGROUND TO THE INVENTION

During surgical procedures it is possible for blood and other body fluids to spurt up into the surgeon's face. With the advent of incurable blood carried diseases the need for surgeon's eyes to be protected has increased.

OBJECTS OF THE PRESENT INVENTION

The main object of the present invention is to provide inexpensive protective eyewear which can be used once and then discarded.

A further object of the present invention is to provide protective eyewear which provides for adequate ventilation to the space between the eyewear and the wearer's face.

BRIEF DESCRIPTION OF THE INVENTION

According to one aspect of the present invention there is provided protective eyewear comprising a sheet of transparent synthetic plastics material, means for attaching said sheet to the wearer with a viewing area of said sheet extending across the wearer's eyes, and protrusion which extends along the upper edge of the rear face of said sheet and which engages the wearer's forehead and holds said viewing area away from the wearer's eyes.

Said protrusion can in one form comprise a strip of foamed synthetic plastics material adhered to said sheet. In another form said protrusion comprises an extension of said sheet which is curled into the form of a roll. Said extension can be fastened into the form of a roll by means of adhesive. In an alternative construction said extension includes a locking tab with locking edges and said sheet has a slit in it, said locking tab being pushed through said slit as the extension is rolled and said locking edges thereafter engaging said sheet to prevent the tab being pulled through the slit in the opposite direction.

In yet another form said protrusion comprises a corrugated strip which is attached to said sheet at the crest of each of its corrugations, said strip and said sheet bounding a series of vertically extending ventilation passages.

To provide improved ventilation said sheets can be formed with slits which extend generally transversely with respect to said upper edge and which lie between said viewing area and end edges of said sheet.

According to a further aspect of the present invention there is provided protective eyewear comprising a sheet of transparent synthetic plastics material, means for attaching said sheet to the wearer with a viewing area of said sheet extending across the wearer's eyes, and ventilation slits between said viewing area and vertically extending side edges of said sheet.

BRIEF DESCRIPTION OF THE DRAWINGS

For a better understanding of the present invention, and to show how the same may be carried into effect, reference will now be made, by way of example, to the accompanying drawings in which.

Figure 1:
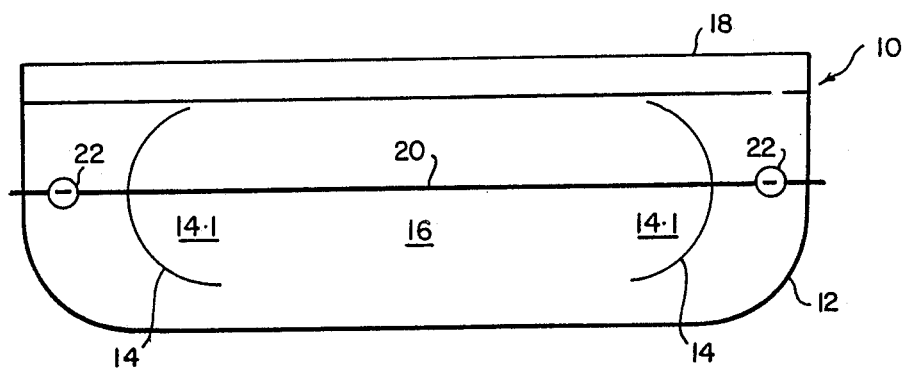
FIG. 1 is an elevation of a first form of protective eyewear.
Figure 2:
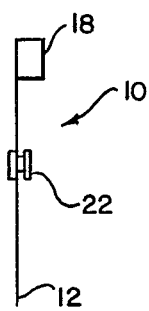
FIG. 2 is an end view of the eyewear of FIG. 1.

DETAILED DESCRIPTION OF THE DRAWINGS:

Referring firstly to FIGS. 1 and 2, the protective eyewear illustrated is generally designated 10 and comprises a sheet 12 of transparent synthetic plastics material. The polyester material which is commercially available under the name "Mylar" is suitable. It is coated with an anti-fogging compound thereby to minimize misting-up of the eyewear in use. The sheet 12 has two C-shaped slits 14 therein, the slits being close to the ends of the sheet 12 and there being between them an uninterrupted viewing area 16. Two flaps 14.1 are formed by the slits 14, the flaps 14.1 forming outward continuations of the area 16.

A strip 18 of foamed synthetic plastics material is adhered to the sheet 12 along the top edge thereof. An elastic band 20 has its ends secured to the sheet 12 by means of two studs 22 which pass through the sheet 12.

The protective eyewear illustrated is intended to be used by surgeons and other medical practitioners whilst they work, the eyewear preventing bone chips, blood and any other body fluids from getting into their eyes. It will understood that, above the eyewear, the surgeon is generally protected by a cap and, below the eyewear, the surgeon has on a mask.

The eyewear is used by pulling the band 20 away from the sheet 12 so that the sheet 12 and the band 20 both bow. The elliptically shaped eyewear can then be pulled down by the surgeon over his head so that the band 20 passes around the back of his head and the sheet 12 lies across his face at the level of his eyes. He is thus able to see through the viewing area 16.

The sheet 12, whilst the eyewear is being worn, has a slightly bowed configuration. The flaps 14.1 tend to remain co-planer with the area 16 rather that curling around the head of the wearer with the portions of the sheet 12 which are outwardly of the slits 14. Thus the slits 14 open up and provide for ventilation from each side to the space behind the area 16.

The slits 14 also facilitate the use of the protective eyewear over spectacles. When spectacles are worn under the eyewear, the outer parts of the spectacle frame lie behind the flaps 14.1 instead of distorting the eyewear.

Figure 3:
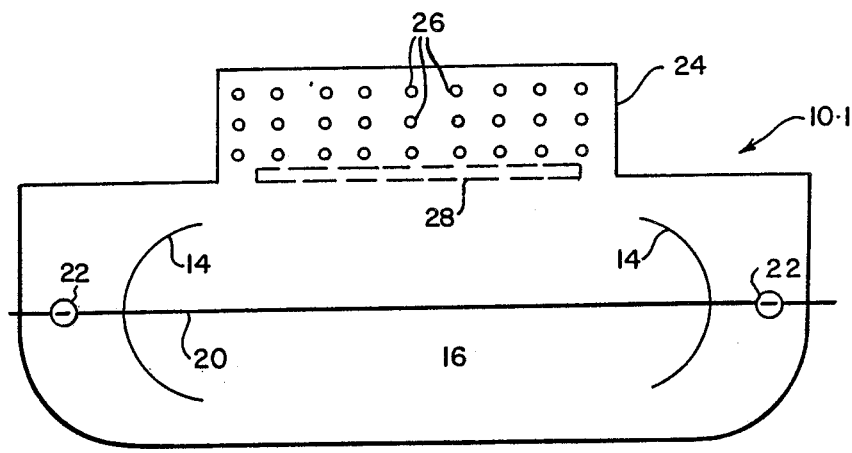
FIG. 3 is an elevation of a second form of protective eyewear.
Figure 4:
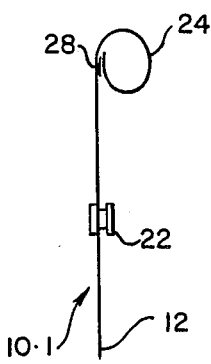
FIG. 4 is an end elevation of the eyewear of FIG. 3 in a somewhat different condition.

The eyewear 10.1 of FIGS. 3 and 4 is similar to the embodiment of FIGS. 1 and 2 and, where applicable, like reference numerals have been used to designate like parts. In the embodiment of FIGS. 3 and 4, the strip 14 is omitted and the sheet 12 has a generally rectangular extension 24. Perforations 26 are formed in the extension 24.

To use the eyewear 10.1 of FIG. 3, adhesive is applied to the area designated 28 and the extension formed into a roll, the free edge of the extension 24 being attached to the area 28. The eyewear is now as shown in FIG. 4. The rolled extension 24 is ventilated both through its ends and through the perforations 26 which are arranged so as to register when the extension 24 is rolled. As the rolled extension 24 does not extend the full length of the eyewear there is also ventilation from above to the areas on each side of the rolled extension 24.

An alternative to the use of adhesive is to heatseal the roll to the remainder of the frame. A heated bar or an ultrasonic horn can be used for this purpose.

Figure 6:
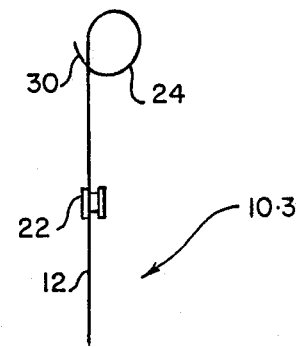
FIG. 6 is an end elevation of the eyewear of FIG. 5 in a different condition.
Figure 5:
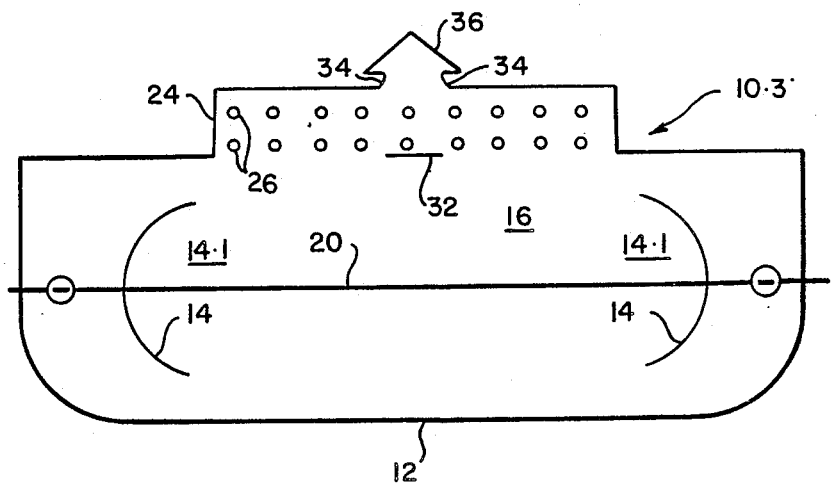
FIG. 5 is an elevation of a third form of protective eyewear.

The protective eyewear 10.3 of FIGS. 5 and 6 is similar to that of FIGS. 3 and 4 except in that an arrow-head-shaped locking tab 30 protrudes from the free edge of the extension 24. A slit 32 is formed where the extension 24 joins the remainder of the sheet 12, the length of the slit being equal to the width of the tab 30 in the regions of the undercuts designated 34. The undercuts 34 result in the tab 30 having opposed locking edges 36.

When the extension 24 of the eyewear of FIGS. 5 and 6 is rolled, the tab 30 is pushed through the slit 32. The wings adjacent the undercuts 34 are deformed towards one another to allow the head of the tab 30 to pass through the slit 32. The wings then spring back to their original position and the locking edges 36 prevent the tab 30 pulling back through the slits 32. Thus the extension 24 is held in its rolled condition without necessitating the use of adhesive.

Figure 7:
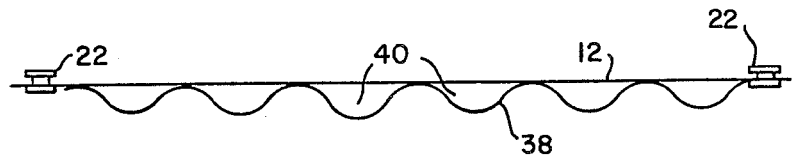
FIG. 7 is a top plan view of a further form of protective eyewear.

In FIG. 7 the sheet 12 has attached thereto a strip 38 of synthetic plastics material, the strip extending across the upper edge of the sheet 12 in the same way that the foam strip 18 does in FIGS. 1 and 2. The strip 38 can extend the full width of the sheet 12 or only across the centre portion of it as do the extensions 24 of FIGS. 3 and 5. The strip 38 and sheet 12 bound a series of vertically extending ventilation passages 40.

The foamed plastics strip 18, the rolled extensions 24 and the strip 38 all have the function of holding the area 16 away from the eyes of the wearer thereby enhancing ventilation but, in addition, holding the area 16 clear of the eyes so that, should the wearer blink or close his eyes, his eyelashes do not encounter the area 16. The strip 18 has the additional function of preventing perspiration from running from the forehead into the wearer's eyes.

I claim:

1. Protective eyewear comprising a sheet of transparent synthetic plastics material, said sheet having an upper edge, a lower edge and two side edges, means for attaching said sheet to the wearer with a viewing area of said sheet extending across the wearer's eyes, a protrusion which extends along the upper edge of the rear face of said sheet and which contacts the wearer's forehead and holds said viewing area away from the wearer's eyes and a flap on each side of said viewing area, said flaps being joined to and forming lateral extensions of said viewing area and each being bounded by a slit in said sheet material, each slit extending along the top and bottom edges of the respective flap and along the laterally outer edge of the flap between the flap and the adjacent one of said side edges.

2. Protective eyewear according to claim 1, in which said protrusion comprises a corrugated strip which is attached to said sheet at the crest of each of its corrugations, said strip and said sheet bounding a series of vertically extending ventilation passages.

3. Protective eyewear comprising
a flat sheet of transparent plastic material having an uninterrupted viewing area and a pair of slits, each said slit being disposed on one side of said viewing area to define a flap extending outwardly of said viewing area;
said sheet being bendable into a bowed shape to lie across a face of a wearer with each flap tending to remain co-planar with said viewing area to provide ventilation to a space between said viewing area and the face of the wearer.

4. Protective eyewear as set forth in claim 3 which further comprises a band secured at opposite ends to said sheet laterally outwardly of said slits for securing said sheet about the face of a wearer.

5. Protective eyewear as set forth in claim 3 wherein said sheet has a perforated extension extending from said viewing area for forming into a roll to hold said viewing area in spaced relation to the eyes of a wearer.

6. Protective eyewear as set forth in claim 5 wherein said sheet has a central slit and said extension has an arrow-headed tab for engaging in said central slit.

7. Protective eyewear as set forth in claim 3 which further comprises a corrugated strip secured to said sheet adjacent and over said viewing area to define vertical ventillation passages.

* * * * *